US012594376B2

(12) United States Patent
Cardinali

(10) Patent No.: US 12,594,376 B2
(45) Date of Patent: Apr. 7, 2026

(54) COMPACT POSITIVE DISPLACEMENT PUMP FOR WEARABLE DRUG DELIVERY DEVICE

(71) Applicant: Insulet Corporation, Acton, MA (US)

(72) Inventor: Steven Cardinali, Tewksbury, MA (US)

(73) Assignee: INSULET CORPORATION, Acton, MA (US)

( * ) Notice: Subject to any disclaimer, the term of this patent is extended or adjusted under 35 U.S.C. 154(b) by 944 days.

(21) Appl. No.: 17/749,463

(22) Filed: May 20, 2022

(65) Prior Publication Data

US 2022/0370709 A1     Nov. 24, 2022

Related U.S. Application Data

(60) Provisional application No. 63/191,436, filed on May 21, 2021.

(51) Int. Cl.
*A61M 5/142* (2006.01)
*A61M 5/315* (2006.01)

(52) U.S. Cl.
CPC .... *A61M 5/14248* (2013.01); *A61M 5/14216* (2013.01); *A61M 5/31511* (2013.01); *A61M 5/31528* (2013.01)

(58) Field of Classification Search
CPC .......... A61M 5/14248; A61M 5/14216; A61M 2005/14252; A61M 2005/31518;
(Continued)

(56) References Cited

U.S. PATENT DOCUMENTS

| | | | |
|---|---|---|---|
| 1,441,508 A | 1/1923 | Jensen | |
| 2,198,666 A | 4/1940 | Gruskin | |

(Continued)

FOREIGN PATENT DOCUMENTS

| | | | |
|---|---|---|---|
| CA | 606281 A | 10/1960 | |
| CN | 1375338 A | 10/2002 | |

(Continued)

OTHER PUBLICATIONS

International Search Report and Written Opinion, Application No. PCT/US2022/016713, mailed Aug. 5, 2022, 19 pages.
(Continued)

*Primary Examiner* — James D Ponton
(74) *Attorney, Agent, or Firm* — GOODWIN PROCTER LLP

(57) ABSTRACT

Embodiments of the present disclosure relate to techniques, processes, devices or systems for pump devices. In one approach, a wearable drug delivery device may include a reservoir configured to store a liquid drug, the reservoir including a housing including an outer wall defining an interior chamber, a sealing member, and a slit through the housing, wherein the sealing member is configured to seal the slit. The wearable drug delivery device may further include a delivery pump device including a drive mechanism coupled to the reservoir for driving the liquid drug out of the reservoir, the drive mechanism including a piston head disposed within the interior chamber of the housing, and a lead screw coupled to a drive nut, wherein the drive nut comprises a blade adjacent the piston head, and wherein the blade is positionable through the slit of the housing.

15 Claims, 7 Drawing Sheets

(58) Field of Classification Search
CPC ........ A61M 2205/50; A61M 2230/005; A61M 2230/201; A61M 5/3272; A61M 5/31528; A61M 5/14236
See application file for complete search history.

(56) References Cited

U.S. PATENT DOCUMENTS

| | | | |
|---|---|---|---|
| 2,752,918 A | 7/1956 | Uytenbogaar |
| 3,176,712 A | 4/1965 | Ramsden |
| 3,297,260 A | 1/1967 | Barlow |
| 3,464,359 A | 9/1969 | King |
| 3,885,662 A | 5/1975 | Schaefer |
| 3,946,732 A | 3/1976 | Hurscham |
| 3,947,692 A | 3/1976 | Payne |
| 3,993,061 A | 11/1976 | OLeary |
| 4,108,177 A | 8/1978 | Pistor |
| 4,152,098 A | 5/1979 | Moody et al. |
| 4,210,173 A | 7/1980 | Choksi et al. |
| 4,221,219 A | 9/1980 | Tucker |
| 4,257,324 A | 3/1981 | Stefansson et al. |
| 4,268,150 A | 5/1981 | Chen |
| 4,277,226 A | 7/1981 | Archibald |
| 4,313,439 A | 2/1982 | Babb et al. |
| 4,371,790 A | 2/1983 | Manning et al. |
| 4,417,889 A | 11/1983 | Choi |
| 4,424,720 A | 1/1984 | Bucchianeri |
| 4,435,173 A | 3/1984 | Siposs et al. |
| 4,475,905 A | 10/1984 | Himmelstrup |
| 4,498,843 A | 2/1985 | Schneider et al. |
| 4,507,115 A | 3/1985 | Kambara et al. |
| 4,551,134 A | 11/1985 | Slavik et al. |
| 4,562,751 A | 1/1986 | Nason et al. |
| 4,567,549 A | 1/1986 | Lemme |
| 4,585,439 A | 4/1986 | Michel |
| 4,601,707 A | 7/1986 | Albisser et al. |
| 4,634,427 A | 1/1987 | Hannula et al. |
| 4,671,429 A | 6/1987 | Spaanderman et al. |
| 4,678,408 A | 7/1987 | Nason et al. |
| 4,684,368 A | 8/1987 | Kenyon |
| 4,685,903 A | 8/1987 | Cable et al. |
| 4,755,169 A | 7/1988 | Sarnoff et al. |
| 4,766,889 A | 8/1988 | Trick et al. |
| 4,808,161 A | 2/1989 | Kamen |
| 4,846,797 A | 7/1989 | Howson et al. |
| 4,858,619 A | 8/1989 | Toth |
| 4,898,579 A | 2/1990 | Groshong et al. |
| 4,908,017 A | 3/1990 | Howson et al. |
| 4,944,659 A | 7/1990 | Labbe et al. |
| 4,969,874 A | 11/1990 | Michel et al. |
| 4,991,743 A | 2/1991 | Walker |
| 5,007,458 A | 4/1991 | Marcus et al. |
| 5,020,325 A | 6/1991 | Henault |
| 5,062,841 A | 11/1991 | Siegel |
| 5,147,311 A | 9/1992 | Pickhard |
| 5,178,609 A | 1/1993 | Ishikawa |
| 5,205,819 A | 4/1993 | Ross et al. |
| 5,213,483 A | 5/1993 | Flaherty et al. |
| 5,222,362 A | 6/1993 | Maus et al. |
| 5,236,416 A | 8/1993 | McDaniel et al. |
| 5,261,882 A | 11/1993 | Sealfon |
| 5,261,884 A | 11/1993 | Stern et al. |
| 5,277,338 A | 1/1994 | Divall et al. |
| 5,281,202 A | 1/1994 | Weber et al. |
| 5,346,476 A | 9/1994 | Elson |
| 5,364,342 A | 11/1994 | Beuchat et al. |
| 5,368,570 A | 11/1994 | Thompson et al. |
| 5,388,615 A | 2/1995 | Edlund et al. |
| 5,433,710 A | 7/1995 | VanAntwerp et al. |
| 5,503,628 A | 4/1996 | Fetters et al. |
| 5,520,661 A | 5/1996 | Lal et al. |
| 5,533,389 A | 7/1996 | Kamen et al. |
| 5,582,593 A | 12/1996 | Hultman |
| 5,618,269 A | 4/1997 | Jacobsen et al. |
| 5,628,309 A | 5/1997 | Brown |
| 5,637,095 A | 6/1997 | Nason et al. |
| 5,665,070 A | 9/1997 | McPhee |
| 5,713,875 A | 2/1998 | Tanner, II |
| 5,747,350 A | 5/1998 | Sattler |
| 5,748,827 A | 5/1998 | Holl et al. |
| 5,776,103 A | 7/1998 | Kriesel et al. |
| 5,779,676 A | 7/1998 | Kriesel et al. |
| 5,785,688 A | 7/1998 | Joshi et al. |
| 5,797,881 A | 8/1998 | Gadot |
| 5,800,397 A | 9/1998 | Wilson et al. |
| 5,807,075 A | 9/1998 | Jacobsen et al. |
| 5,839,467 A | 11/1998 | Saaski et al. |
| 5,891,097 A | 4/1999 | Saito et al. |
| 5,897,530 A | 4/1999 | Jackson |
| 5,906,592 A | 5/1999 | Kriesel et al. |
| 5,906,597 A | 5/1999 | McPhee |
| 5,911,716 A | 6/1999 | Rake et al. |
| 5,919,167 A | 7/1999 | Mulhauser et al. |
| 5,957,890 A | 9/1999 | Mann et al. |
| 5,961,492 A | 10/1999 | Kriesel et al. |
| 5,971,963 A | 10/1999 | Choi |
| 6,019,747 A | 2/2000 | McPhee |
| 6,050,457 A | 4/2000 | Arnold et al. |
| 6,068,615 A | 5/2000 | Brown et al. |
| 6,159,188 A | 12/2000 | Laibovitz et al. |
| 6,174,300 B1 | 1/2001 | Kriesel et al. |
| 6,190,359 B1 | 2/2001 | Heruth |
| 6,200,293 B1 | 3/2001 | Kriesel et al. |
| 6,352,522 B1 | 3/2002 | Kim et al. |
| 6,363,609 B1 | 4/2002 | Pickren |
| 6,375,638 B2 | 4/2002 | Nason et al. |
| 6,474,219 B2 | 11/2002 | Klitmose et al. |
| 6,485,461 B1 | 11/2002 | Mason et al. |
| 6,485,462 B1 | 11/2002 | Kriesel |
| 6,488,652 B1 | 12/2002 | Weijand et al. |
| 6,520,936 B1 | 2/2003 | Mann |
| 6,527,744 B1 | 3/2003 | Kriesel et al. |
| 6,537,249 B2 | 3/2003 | Kriesell et al. |
| 6,539,286 B1 | 3/2003 | Jiang |
| 6,569,115 B1 | 5/2003 | Barker et al. |
| 6,595,956 B1 | 7/2003 | Gross et al. |
| 6,656,158 B2 | 12/2003 | Mahoney et al. |
| 6,699,218 B2 | 3/2004 | Flaherty et al. |
| 6,723,072 B2 | 4/2004 | Flaherty et al. |
| 6,740,059 B2 | 5/2004 | Flaherty |
| 6,749,407 B2 | 6/2004 | Xie et al. |
| 6,800,071 B1 | 10/2004 | McConnell et al. |
| 6,851,260 B2 | 2/2005 | Mernoe |
| 6,883,778 B1 | 4/2005 | Newton et al. |
| 7,018,360 B2 | 3/2006 | Flaherty et al. |
| 7,104,275 B2 | 9/2006 | Dille |
| 7,128,727 B2 | 10/2006 | Flaherty et al. |
| 7,137,964 B2 | 11/2006 | Flaherty |
| 7,160,272 B1 | 1/2007 | Eyal et al. |
| 7,303,549 B2 | 12/2007 | Flaherty |
| 7,771,392 B2 | 8/2010 | De Polo et al. |
| 7,914,499 B2 | 3/2011 | Gonnelli et al. |
| 7,951,114 B2 | 5/2011 | Rush et al. |
| 8,267,921 B2 | 9/2012 | Yodfat et al. |
| 8,382,703 B1 | 2/2013 | Abdelaal |
| 8,499,913 B2 | 8/2013 | Gunter |
| 8,734,396 B2 | 5/2014 | Wyss |
| 8,905,995 B2 | 12/2014 | Mernoe |
| 8,920,376 B2 | 12/2014 | Caffey et al. |
| 8,939,935 B2 | 1/2015 | OConnor et al. |
| 9,180,244 B2 | 11/2015 | Anderson et al. |
| 9,192,716 B2 | 11/2015 | Jugl et al. |
| 9,402,950 B2 | 8/2016 | Dilanni et al. |
| 9,539,596 B2 | 1/2017 | Ikushima |
| 10,441,723 B2 | 10/2019 | Nazzaro |
| 10,695,485 B2 | 6/2020 | Nazzaro |
| 2001/0016710 A1 | 8/2001 | Nason et al. |
| 2001/0056258 A1 | 12/2001 | Evans |
| 2002/0029018 A1 | 3/2002 | Jeffrey |
| 2002/0032374 A1 | 3/2002 | Holker et al. |
| 2002/0037221 A1 | 3/2002 | Mastrangelo et al. |
| 2002/0173769 A1 | 11/2002 | Gray et al. |
| 2002/0173830 A1 | 11/2002 | Starkweather et al. |
| 2003/0040715 A1 | 2/2003 | DAntonio et al. |
| 2003/0055380 A1 | 3/2003 | Flaherty |

(56)  References Cited

U.S. PATENT DOCUMENTS

| | | |
|---|---|---|
| 2003/0097092 A1 | 5/2003 | Flaherty |
| 2003/0109827 A1 | 6/2003 | Lavi et al. |
| 2003/0163097 A1 | 8/2003 | Fleury et al. |
| 2003/0198558 A1 | 10/2003 | Nason et al. |
| 2003/0199825 A1 | 10/2003 | Flaherty |
| 2004/0010207 A1 | 1/2004 | Flaherty et al. |
| 2004/0064088 A1 | 4/2004 | Gorman et al. |
| 2004/0068224 A1 | 4/2004 | Couvillon, Jr. et al. |
| 2004/0069044 A1 | 4/2004 | Lavi et al. |
| 2004/0092865 A1 | 5/2004 | Flaherty et al. |
| 2004/0094733 A1 | 5/2004 | Hower et al. |
| 2004/0115068 A1 | 6/2004 | Hansen et al. |
| 2004/0153032 A1 | 8/2004 | Garribotto et al. |
| 2005/0020980 A1 | 1/2005 | Inoue et al. |
| 2005/0165363 A1 | 7/2005 | Judson et al. |
| 2005/0203461 A1 | 9/2005 | Flaherty et al. |
| 2005/0238507 A1 | 10/2005 | Dilanni et al. |
| 2005/0273059 A1 | 12/2005 | Mernoe |
| 2005/0277882 A1 | 12/2005 | Kriesel |
| 2006/0041229 A1 | 2/2006 | Garibotto et al. |
| 2006/0079765 A1 | 4/2006 | Neer et al. |
| 2006/0155210 A1 | 7/2006 | Beckman et al. |
| 2006/0173439 A1 | 8/2006 | Thorne et al. |
| 2006/0178633 A1 | 8/2006 | Garibotto et al. |
| 2006/0253085 A1 | 11/2006 | Geismar et al. |
| 2006/0282290 A1 | 12/2006 | Flaherty et al. |
| 2007/0005018 A1 | 1/2007 | Tekbuchava |
| 2007/0073236 A1 | 3/2007 | Merno et al. |
| 2007/0088271 A1 | 4/2007 | Richards |
| 2007/0118405 A1 | 5/2007 | Campbell et al. |
| 2007/0255260 A1 | 11/2007 | Haase |
| 2007/0282269 A1 | 12/2007 | Carter et al. |
| 2008/0004515 A1 | 1/2008 | Jennewine |
| 2008/0051738 A1 | 2/2008 | Griffin |
| 2008/0114304 A1 | 5/2008 | Nalesso et al. |
| 2008/0172028 A1 | 7/2008 | Blomquist |
| 2008/0243211 A1 | 10/2008 | Cartwright et al. |
| 2008/0294040 A1 | 11/2008 | Mohiuddin et al. |
| 2009/0024083 A1 | 1/2009 | Kriesel et al. |
| 2009/0062767 A1 | 3/2009 | Van Antwerp et al. |
| 2009/0198215 A1 | 8/2009 | Chong et al. |
| 2009/0278875 A1 | 11/2009 | Holm et al. |
| 2009/0326472 A1 | 12/2009 | Carter et al. |
| 2010/0036326 A1 | 2/2010 | Matusch |
| 2010/0152658 A1 | 6/2010 | Hanson et al. |
| 2010/0241066 A1 | 9/2010 | Hansen et al. |
| 2011/0054399 A1 | 3/2011 | Chong et al. |
| 2011/0073620 A1 | 3/2011 | Verrilli |
| 2011/0108158 A1 | 5/2011 | Huwiler et al. |
| 2011/0144586 A1 | 6/2011 | Michaud et al. |
| 2011/0180480 A1 | 7/2011 | Kloeffel et al. |
| 2011/0213329 A1 | 9/2011 | Yodfat et al. |
| 2011/0230833 A1 | 9/2011 | Landman et al. |
| 2011/0319814 A1 | 12/2011 | Sullivan et al. |
| 2012/0078161 A1 | 3/2012 | Masterson et al. |
| 2012/0172817 A1 | 7/2012 | Bruggemann et al. |
| 2012/0209207 A1 | 8/2012 | Gray et al. |
| 2013/0006213 A1 | 1/2013 | Arnitz et al. |
| 2013/0017099 A1 | 1/2013 | Genoud |
| 2013/0064701 A1 | 3/2013 | Konishi |
| 2013/0177455 A1 | 7/2013 | Kamen et al. |
| 2013/0178803 A1 | 7/2013 | Raab |
| 2013/0245545 A1 | 9/2013 | Arnold et al. |
| 2013/0267932 A1 | 10/2013 | Franke et al. |
| 2013/0296792 A1 | 11/2013 | Cabiri |
| 2014/0018730 A1 | 1/2014 | Muller-Pathle |
| 2014/0127048 A1 | 5/2014 | Dilanni et al. |
| 2014/0128839 A1 | 5/2014 | Dilanni et al. |
| 2014/0142508 A1 | 5/2014 | Dilanni et al. |
| 2014/0148784 A1 | 5/2014 | Anderson et al. |
| 2014/0171901 A1 | 6/2014 | Langsdorf et al. |
| 2014/0214001 A1 | 7/2014 | Mortazavi |
| 2015/0041498 A1 | 2/2015 | Kakiuchi et al. |
| 2015/0051487 A1 | 2/2015 | Uber et al. |
| 2015/0057613 A1 | 2/2015 | Clemente et al. |
| 2015/0064036 A1 | 3/2015 | Eberhard |
| 2015/0137017 A1 | 5/2015 | Ambrosina et al. |
| 2015/0202386 A1 | 7/2015 | Brady et al. |
| 2015/0273133 A1* | 10/2015 | Kerschbaumer .... A61M 5/3129 |
| | | 53/469 |
| 2015/0290389 A1 | 10/2015 | Nessel |
| 2015/0297825 A1 | 10/2015 | Focht et al. |
| 2016/0008549 A1 | 1/2016 | Plumptre et al. |
| 2016/0025544 A1 | 1/2016 | Kamer |
| 2016/0055842 A1 | 2/2016 | Defranks et al. |
| 2016/0082242 A1 | 3/2016 | Burton et al. |
| 2016/0129190 A1 | 5/2016 | Haitsuka |
| 2016/0193423 A1 | 7/2016 | Bilton |
| 2016/0213851 A1 | 7/2016 | Weibel et al. |
| 2017/0021096 A1 | 1/2017 | Cole et al. |
| 2017/0021137 A1 | 1/2017 | Cole |
| 2017/0100541 A1 | 4/2017 | Constantineau et al. |
| 2017/0216516 A1 | 8/2017 | Dale |
| 2017/0239415 A1 | 8/2017 | Hwang et al. |
| 2017/0290975 A1 | 10/2017 | Barmaimon et al. |
| 2018/0021521 A1 | 1/2018 | Sanchez |
| 2018/0185579 A1 | 7/2018 | Joseph et al. |
| 2018/0313346 A1 | 11/2018 | Oakes |
| 2019/0192782 A1 | 6/2019 | Pedersen et al. |
| 2019/0365993 A1 | 12/2019 | Staub et al. |
| 2020/0009315 A1 | 1/2020 | Brouet et al. |
| 2020/0345931 A1 | 11/2020 | Gray et al. |
| 2023/0285663 A1* | 9/2023 | Varma ................. A61M 5/3129 |

FOREIGN PATENT DOCUMENTS

| | | |
|---|---|---|
| CN | 102498292 B | 7/2015 |
| CN | 204972511 U | 1/2016 |
| CN | 105764543 B | 7/2016 |
| CN | 206175149 U | 5/2017 |
| CN | 107096091 A | 8/2017 |
| CN | 108472441 A | 8/2018 |
| DE | 4200595 A1 | 7/1993 |
| DE | 19723648 C1 | 8/1998 |
| DE | 102005040344 A1 | 3/2007 |
| EP | 0454331 A1 | 10/1991 |
| EP | 0789146 A1 | 8/1997 |
| EP | 867196 A2 | 9/1998 |
| EP | 1065378 A2 | 1/2001 |
| EP | 1177802 A1 | 2/2002 |
| EP | 1403519 A1 | 3/2004 |
| EP | 2229970 A1 | 9/2010 |
| EP | 2397181 A1 | 12/2011 |
| EP | 2468338 A1 | 6/2012 |
| EP | 2556815 A1 | 2/2013 |
| EP | 2703024 A1 | 3/2014 |
| EP | 1874390 B1 | 10/2014 |
| EP | 2830499 A1 | 2/2015 |
| EP | 3656418 A1 | 5/2020 |
| FR | 2096275 A5 | 2/1972 |
| FR | 2455269 A1 | 11/1980 |
| FR | 2507637 A1 | 12/1982 |
| FR | 2731475 A1 | 9/1996 |
| GB | 357139 A | 9/1931 |
| GB | 810488 A | 3/1959 |
| GB | 875034 A | 8/1961 |
| GB | 1204836 A | 9/1970 |
| GB | 2008806 A | 6/1979 |
| GB | 2077367 A | 12/1981 |
| GB | 2456681 A | 7/2009 |
| GB | 2549750 A | 11/2017 |
| IL | 46017 A | 11/1977 |
| JP | 06063133 A | 3/1994 |
| JP | 106296690 A | 10/1994 |
| JP | H08238324 A | 9/1996 |
| JP | 2004247271 A | 9/2004 |
| JP | 2004274719 A | 9/2004 |
| JP | 2005188355 A | 7/2005 |
| JP | 2005523127 A | 8/2005 |
| JP | 2006159228 A | 6/2006 |
| JP | 6098988 B2 | 9/2006 |
| JP | 2006249130 A | 9/2006 |
| JP | 2009514580 A | 4/2009 |
| JP | 2017513577 A | 6/2017 |

(56)  References Cited

FOREIGN PATENT DOCUMENTS

| | | | |
|---|---|---|---|
| JP | 2021500102 | A | 1/2021 |
| NL | 1019126 | C1 | 4/2003 |
| WO | 8101658 | A1 | 6/1981 |
| WO | 8606796 | A1 | 11/1986 |
| WO | 9320864 | A1 | 10/1993 |
| WO | 9415660 | A1 | 7/1994 |
| WO | 9855073 | A1 | 12/1998 |
| WO | 9856293 | A1 | 12/1998 |
| WO | 9910040 | A1 | 3/1999 |
| WO | 9910049 | A1 | 3/1999 |
| WO | 9962576 | A1 | 12/1999 |
| WO | 0029047 | A1 | 5/2000 |
| WO | 0178812 | A1 | 10/2001 |
| WO | 0220073 | A2 | 3/2002 |
| WO | 0226282 | A2 | 4/2002 |
| WO | 2002076535 | A1 | 4/2002 |
| WO | 2003097133 | A1 | 4/2002 |
| WO | 02068823 | A1 | 9/2002 |
| WO | 2004032994 | A2 | 4/2004 |
| WO | 2004056412 | A2 | 7/2004 |
| WO | 2004110526 | A1 | 12/2004 |
| WO | 2007066152 | A2 | 6/2007 |
| WO | 2008133702 | A1 | 11/2008 |
| WO | 2009039203 | A2 | 3/2009 |
| WO | 2009141005 | A1 | 11/2009 |
| WO | 2010022069 | A2 | 2/2010 |
| WO | 2010077279 | A1 | 7/2010 |
| WO | 2010139793 | A1 | 12/2010 |
| WO | 2011010198 | A2 | 1/2011 |
| WO | 2011031458 | A1 | 3/2011 |
| WO | 2011069935 | A2 | 6/2011 |
| WO | 2011075042 | A1 | 6/2011 |
| WO | 2011133823 | A1 | 10/2011 |
| WO | 2012065780 | A2 | 5/2012 |
| WO | 2012073032 | A1 | 6/2012 |
| WO | 2013050535 | A2 | 4/2013 |
| WO | 2013137893 | A1 | 9/2013 |
| WO | 2013149186 | A1 | 10/2013 |
| WO | 2014029416 | A1 | 2/2014 |
| WO | 2014149357 | A1 | 9/2014 |
| WO | 2014179774 | A1 | 11/2014 |
| WO | 2015032772 | A1 | 3/2015 |
| WO | 2015048791 | A1 | 4/2015 |
| WO | 2015081337 | A2 | 6/2015 |
| WO | 2015117854 | A1 | 8/2015 |
| WO | 2015167201 | A1 | 11/2015 |
| WO | 2015177082 | A1 | 11/2015 |
| WO | 2017148855 | A1 | 9/2017 |
| WO | 2017187177 | A1 | 11/2017 |
| WO | 2020104872 | A1 | 5/2020 |
| WO | 2021016452 | A1 | 1/2021 |

OTHER PUBLICATIONS

International Search Report and Written Opinion for International Patent Application No. PCT/US2022/029012, mailed Aug. 19, 2022, 12 pages.
International Search Report and Written Opinion, Application No. PCT/US2022/030192, mailed Aug. 12, 2022, 14 pages.
International Search Report and Written Opinion for PCT/US2018/014351, mailed on Jun. 4, 2018, 9 pages.
Lind et al. "Linear Motion Miniature Actuators." Paper presented at the 2nd Tampere International Conference on Machine Automation, Tampere, Finland (Sep. 1998).
Author Unknown "The Animas R-1000 Insulin Pump—Animas Corporation intends to exit the insulin pump businessand discontinue the manufacturing and sale of Animas® Vibe® and One Touch Ping® insulin pumps." [online], Dec. 1999 [retrieved on Jan. 8, 2019]. Retrieved from the Internet URL: http://www.animaspatientsupport.com/.
Author Unknown, CeramTec "Discover the Electro Ceramic Products CeramTec acquired from Morgan AdvancedMaterials" [online],
Mar. 1, 2001 [retrieved on Jan. 8, 2019. Retrieved from the Internet URL: http://www.morgantechnicalceramics.com/.
Vaughan, M.E., "The Design, Fabrication, and Modeling of a Piezoelectric Linear Motor." Master's thesis, Virginia Polytechnic Institute and State University, VA. (2001).
Galante et al., "Design, Modeling, and Performance of a High Force Piezoelectric Inchworm Motor," Journal of Intelligent Material Systems and Structures, vol. 10, 962-972 (1999).
International Search Report and Written Opinion for International Application No. PCT/US2017/055054, mailed on Jan. 25, 2018, 13 pages.
International Search Report and Written Opinion for International Application No. PCT/US2018/045155, mailed on Oct. 15, 2018, 15 pages.
International Preliminary Report on Patentability for International Application No. PCT/US2017/034811 issued on Nov. 27, 2018, 10 pages.
International Preliminary Report on Patentability for International Patent Application No. PCT/US2017/046508, Feb. 12, 2019, 10 pages.
International Search Report and Written Opinion for International Application No. PCT/US2017/046508, mailed on Jan. 17, 2018, 14 pages.
International Search Report and Written Opinion for International Application No. PCT/US2017/046777, mailed on Dec. 13, 2017, 14 pages.
International Search Report and Written Opinion for International Application No. PCT/US2017/046737, mailed on Dec. 14, 2017, 11 pages.
International Search Report and Written Opinion for International Application No. PCT/US2017/034814, mailed on Oct. 11, 2017, 18 pages.
European Search Report and Written Opinion for the European Patent Application No. EP19177571, dated Oct. 30, 2019, 8 pages.
International Preliminary Report on Patentability for International Patent Application No. PCT/US2018/014351, dated Jul. 23, 2019, 7 pages.
International Preliminary Report on Patentability for International Patent Application No. PCT/US2017/046777, dated Feb. 19, 2019, 8 pages.
International Preliminary Report on Patentability for International Patent Application No. PCT/US2017/046737, dated Feb. 19, 2019, 8 pages.
International Preliminary Report on Patentability for International Patent Application No. PCT/US2017/055054, dated Apr. 9, 2019, 8 pages.
International Search Report and Written Opinion for Application No. PCT/US2017/034811, mailed Oct. 18, 2017, 15 pages.
EPO Search Report received in Application No. 13768938.6, dated Nov. 11, 2015, 8 pages.
International Search Report and Written Opinion for PCT Application No. PCT/US13/34674, mailed Aug. 6, 2013, 17 pages.
International Search Report and Written Opinion for International Application No. PCT/GB2007/004073, Jan. 31, 2008, 8 pages.
International Search Report and Written Opinion for International Patent Application No. PCT/US2019/063615, dated May 3, 2020, 17 pages.
International Preliminary Report on Patentability for International Patent Application No. PCT/US2018/045155, dated Feb. 14, 2020, 10 pages.
International Search Report and Written Opinion for International Patent Application No. PCT/US2019/035756, dated Jul. 31, 2019, 11 pages.
European Search Report and Written Opinion, Application No. EP02768908, dated Apr. 30, 2010.
International Search Report and Written Opinion, Application No. PCT/US2019/042233, mailed Jan. 3, 2020, 14 pages.
International Search Report and Written Opinion, Application No. PCT/US2021/060148, mailed Mar. 17, 2022, 17 pages.
European Search Report and Written Opinion for European Patent Application No. EP20174878, dated Sep. 29, 2020, 4 pages.
Schott web-page image from Jul. 9, 2016, https://www.us.schott.com/pharmaceutical_packaging/english/products/cartridges.html.

(56)      References Cited

OTHER PUBLICATIONS

International Search Report and Written Opinion for International Patent Application No. PCT/US2021/055581, dated Feb. 8, 2022, 19 pages.
International Search Report and Written Opinion for International Patent Application No. PCT/US2022/011356, dated Apr. 29, 2022, 19 pages.
International Search Report and Written Opinion for PCT Application No. PCT/US2019/059854, mailed Aug. 26, 2020, 15 pages.

* cited by examiner

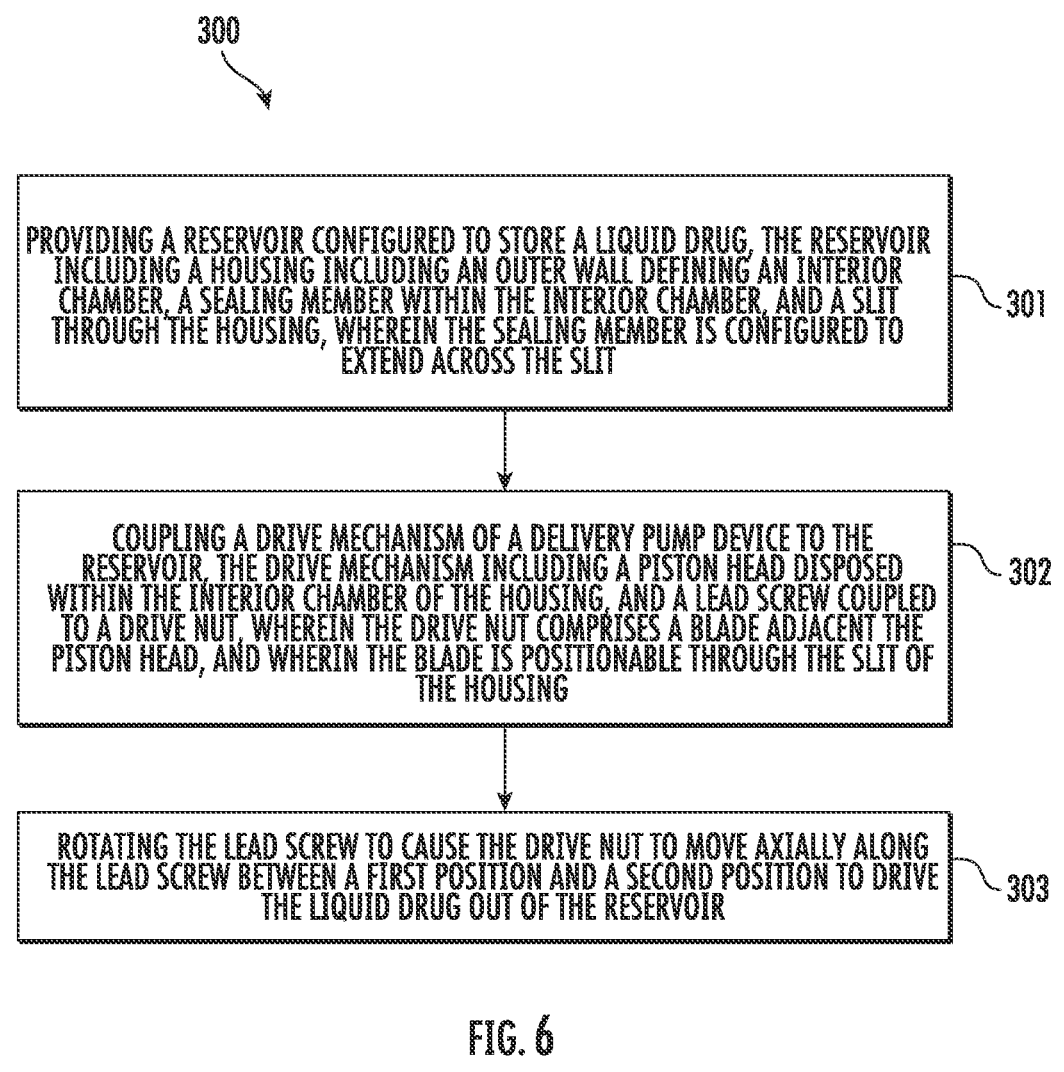

300

PROVIDING A RESERVOIR CONFIGURED TO STORE A LIQUID DRUG, THE RESERVOIR INCLUDING A HOUSING INCLUDING AN OUTER WALL DEFINING AN INTERIOR CHAMBER, A SEALING MEMBER WITHIN THE INTERIOR CHAMBER, AND A SLIT THROUGH THE HOUSING, WHEREIN THE SEALING MEMBER IS CONFIGURED TO EXTEND ACROSS THE SLIT ⟍ 301

COUPLING A DRIVE MECHANISM OF A DELIVERY PUMP DEVICE TO THE RESERVOIR, THE DRIVE MECHANISM INCLUDING A PISTON HEAD DISPOSED WITHIN THE INTERIOR CHAMBER OF THE HOUSING, AND A LEAD SCREW COUPLED TO A DRIVE NUT, WHEREIN THE DRIVE NUT COMPRISES A BLADE ADJACENT THE PISTON HEAD, AND WHERIN THE BLADE IS POSITIONABLE THROUGH THE SLIT OF THE HOUSING ⟍ 302

ROTATING THE LEAD SCREW TO CAUSE THE DRIVE NUT TO MOVE AXIALLY ALONG THE LEAD SCREW BETWEEN A FIRST POSITION AND A SECOND POSITION TO DRIVE THE LIQUID DRUG OUT OF THE RESERVOIR ⟍ 303

FIG. 6

COMPACT POSITIVE DISPLACEMENT PUMP FOR WEARABLE DRUG DELIVERY DEVICE

RELATED APPLICATIONS

This application claims the benefit of U.S. Provisional Patent Application No. 63/191,436, filed May 21, 2021, the contents of which are incorporated herein by reference in their entirety.

TECHNICAL FIELD

The disclosed embodiments generally relate to medication delivery. More particularly, the disclosed embodiments relate to techniques, processes, systems, and dispensing devices for delivering a fluid medicament in a space-efficient manner.

BACKGROUND

Many wearable drug delivery devices include a reservoir for storing a liquid drug. A pump device including a drive mechanism is operated to expel the stored liquid drug from the reservoir for delivery to a user. Some conventional positive displacement pump devices use a plunger of the drive mechanism to expel the liquid drug from the reservoir. Accordingly, the drive mechanism generally has a length equal to a length of the reservoir. When the reservoir is filled, the drive mechanism requires a length of the drug delivery devices to be significantly larger, for example, about twice the length of the reservoir to allow the plunger to traverse the length of the reservoir to expel fluid. Increasing the size of drug delivery devices to accommodate filled reservoirs or pre-filled cartridges and corresponding drive mechanism components leads to bulky devices that are uncomfortable for the user to wear.

Accordingly, there is a need for a simplified system for accurately expelling a liquid drug from a reservoir, which also reduces overall drug delivery device size.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In some approaches, a wearable drug delivery device may include a reservoir configured to store a liquid drug, the reservoir including a housing including an outer wall defining an interior chamber, a sealing member, and a slit through the housing, wherein the sealing member is configured to seal the slit. The wearable drug delivery device may further include a delivery pump device including a drive mechanism coupled to the reservoir for driving the liquid drug out of the reservoir, the drive mechanism including a piston head disposed within the interior chamber of the housing, and a lead screw coupled to a drive nut, wherein the drive nut comprises a blade adjacent the piston head, and wherein the blade is positionable through the slit of the housing.

In some approaches, a wearable drug delivery device may include a reservoir configured to store a liquid drug, the reservoir including a housing having an outer wall defining an interior chamber, a sealing member, and a slit through the housing, wherein the sealing member is configured to seal the slit. The wearable drug delivery device may further include a delivery pump device including a drive mechanism coupled to the reservoir for driving the liquid drug out of the reservoir. The drive mechanism may include a piston head disposed within the interior chamber of the housing, and a lead screw coupled to a drive nut, wherein the drive nut comprises a blade adjacent the piston head, wherein the blade is positionable through the slit of the housing, wherein the lead screw has external threading engaged with corresponding internal threading of the drive nut, wherein rotation of the lead screw causes the blade to move axially along the lead screw.

In some approaches, a method may include providing a reservoir configured to store a liquid drug, the reservoir including a housing including an outer wall defining an interior chamber, a sealing member, and a slit through the housing, wherein the sealing member is configured to seal the slit. The method may further include coupling a drive mechanism of a delivery pump device to the reservoir, the drive mechanism including a piston head disposed within the interior chamber of the housing, and a lead screw coupled to a drive nut, wherein the drive nut comprises a blade adjacent the piston head, and wherein the blade is positionable through the slit of the housing. The method may further include rotating the lead screw to cause the drive nut to move axially along the lead screw between a first position and a second position to drive the liquid drug out of the reservoir.

BRIEF DESCRIPTION OF THE DRAWINGS

In the drawings, like reference characters generally refer to the same parts throughout the different views. In the following description, various embodiments of the present disclosure are described with reference to the following drawings, in which:

FIG. 6 illustrates a process flow of a method according to embodiments of the present disclosure.

Figure 1:
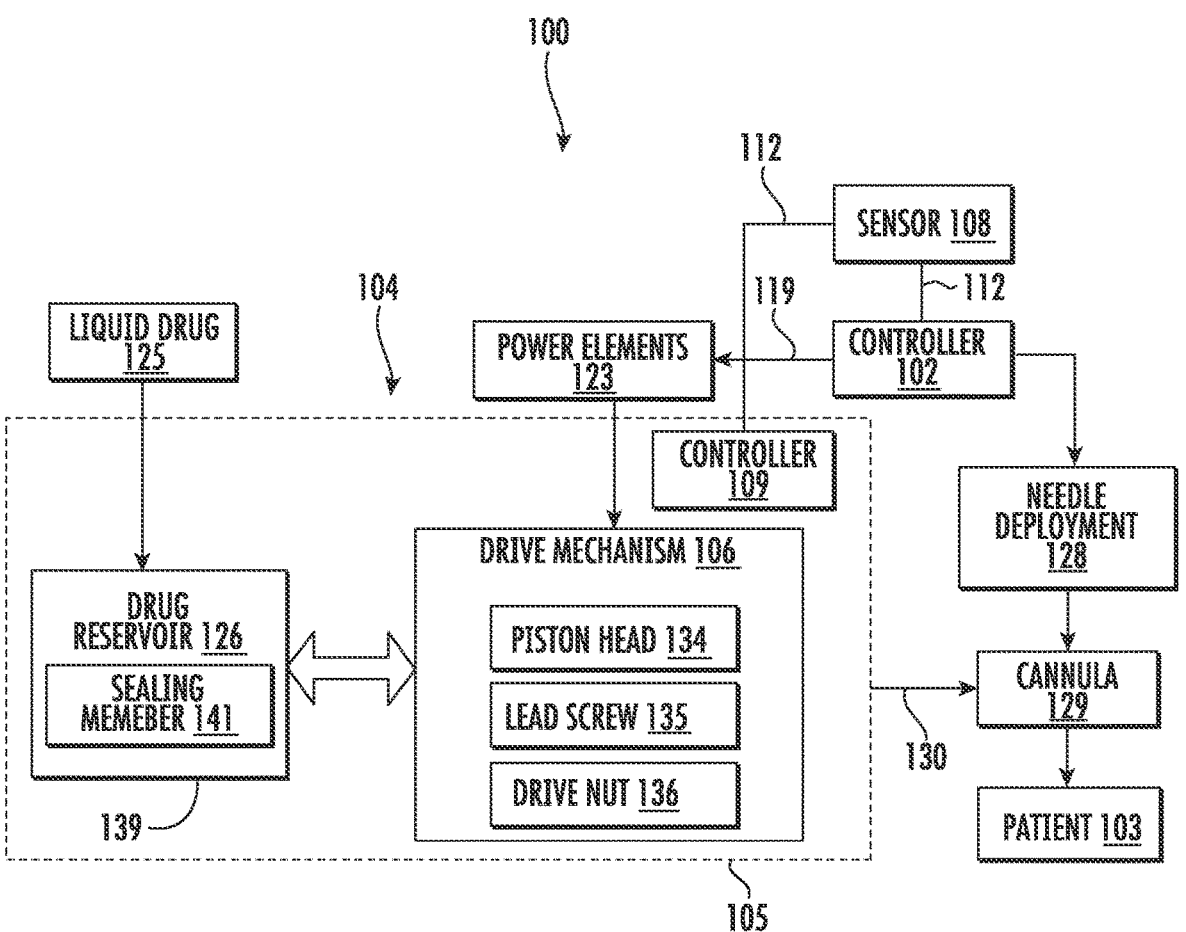
FIG. 1 illustrates a schematic diagram of a drug delivery system according to embodiments of the present disclosure.

The drawings are not necessarily to scale. The drawings are merely representations, not intended to portray specific parameters of the disclosure. The drawings are intended to depict exemplary embodiments of the disclosure, and therefore are not be considered as limiting in scope. Furthermore, certain elements in some of the figures may be omitted, or illustrated not-to-scale, for illustrative clarity. Still furthermore, for clarity, some reference numbers may be omitted in certain drawings.

DETAILED DESCRIPTION

Systems, devices, and methods in accordance with the present disclosure will now be described more fully hereinafter with reference to the accompanying drawings, where one or more embodiments are shown. The systems, devices, and methods may be embodied in many different forms and are not to be construed as being limited to the embodiments set forth herein. Instead, these embodiments are provided so the disclosure will be thorough and complete, and will fully convey the scope of methods and devices to those skilled in the art. Each of the systems, devices, and methods disclosed herein provides one or more advantages over conventional systems, components, and methods.

As mentioned above, there is a goal to provide compact pumping solutions in order to minimize impact to the patient. In the present disclosure, a positive displacement pump leveraging a drive mechanism including a lead screw and drive nut is used to incrementally move a piston head forward. Unlike prior art approaches, which require an overall amount of space for the drive mechanism to be twice the length of the reservoir to allow for the piston plunger to fully extend behind the reservoir when full, embodiments of the present disclosure maintain a position of the plunger relative to the reservoir housing to improve the size impact of the device while maintaining the benefits of the positive displacement pumping methodology.

In some embodiments, a wearable drug delivery device includes a reservoir with a central core shaft having one or more slits through a sidewall thereof. A thin film sealing member may be adhered an exterior and/or interior of the core shaft, wherein the thin film covers the slit(s). A drive mechanism of the wearable drug delivery device may include a piston head having one or more sealing rings (e.g., O-ring), a lead screw extending through the core shaft, and a drive nut coupled to the lead screw. The drive nut may include a blade operable to extend through the slit(s) for breaking the thin film upon contact. To deliver a liquid drug from the reservoir, the lead screw is rotated, which causes the drive nut to move down the lead screw. The blade, or an adjacent portion thereof, of the drive nut transmits a force to the piston head, which pushes the piston head within the reservoir to expel the liquid drug therefrom. In some embodiments, the piston head includes an interior sealing ring, which presses against the thin film and/or the core shaft.

In some embodiments, a drive mechanism may include one or more components positioned external to a housing of the reservoir. For example, the lead screw may be positioned adjacent an exterior surface of an outer wall of the housing, while the drive nut extends between the lead screw and the piston head, which is positioned within an interior chamber of the housing. The drive nut may include one or more blades extending through a slit in the outer wall of the housing. To deliver a liquid drug from the reservoir, the lead screw is rotated, which causes the drive nut to move down the lead screw. The blade(s), or an adjacent portion thereof, of the drive nut transmits a force to the piston head, which pushes the piston head within the reservoir to expel the liquid drug therefrom. The blade cuts through a thin film sealing member, which may be positioned along an interior surface of the outer wall of the housing, to allow the piston head to continue traveling. The sealing member may alternatively be positioned directly within the slit in the outer wall and/or along an outer surface of the outer wall of the housing.

In various embodiments, the wearable drug delivery device described herein may include an analyte sensor, such as a blood glucose sensor, and the cannula or microneedle array may be operable in allowing the device to measure an analyte level in a user of the device.

FIG. 1 illustrates a simplified block diagram of an example system (hereinafter "system") 100. The system 100 may be a wearable or on-body drug delivery device and/or an analyte sensor attached to the skin of a patient 103. The system 100 may include a controller 102, a pump mechanism 104 (hereinafter "pump 104"), and a sensor 108. The sensor 108 may be a glucose or other analyte monitor such as, for example, a continuous glucose monitor, and may be incorporated into the wearable device. The sensor 108 may, for example, be operable to measure blood glucose (BG) values of a user to generate a measured BG level signal 112. The controller 102, the pump 104, and the sensor 108 may be communicatively coupled to one another via a wired or wireless communication path. For example, each of the controller 102, the pump 104 and the sensor 108 may be equipped with a wireless radio frequency transceiver operable to communicate via one or more communication protocols, such as Bluetooth®, or the like. The system 100 may also include a delivery pump device (hereinafter "device") 105, which includes a drive mechanism 106 coupled to a reservoir 126 for driving a liquid drug 125 therefrom. As will be described in greater detail herein, the drive mechanism 106 may include a piston head 134 disposed within an interior chamber of a housing 139 of the reservoir 126, and a lead screw 135 coupled to a drive nut 136. In some embodiments, the drive nut 136 may include a blade adjacent the piston head 134, wherein the blade is positionable through a slit of the housing 139 for engagement with a sealing member 141 located therein. The system 100 may include additional components which are not shown or described for the sake of brevity.

The controller 102 may receive a desired BG level signal, which may be a first signal, indicating a desired BG level or range for the patient 103. The desired BG level signal may be stored in memory of a controller 109 on device 105, received from a user interface to the controller 102, or another device, or by an algorithm within controller 109 (or controller 102) that automatically determines a BG level for the patient 103. The sensor 108 may be coupled to the patient 103 and operable to measure an approximate value of a BG level of the user. In response to the measured BG level or value, the sensor 108 may generate a signal indicating the measured BG value. As shown, the controller 102 may also receive from the sensor 108 via a communication path, the measured BG level signal 112, which may be a second signal.

Based on the desired BG level signal and the measured BG level signal 112, the controller 102 or controller 109 may generate one or more control signals for directing operation of the pump 104. For example, one control signal 119 from the controller 102 or controller 109 may cause the pump 104 to turn on, or activate one or more power elements 123 operably connected with the device 105. The specified amount of the liquid drug 125 may be determined as an appropriate amount of insulin to drive the measured BG level of the user to the desired BG level. Based on operation of the pump 104, as determined by the control signal 119, the patient 103 may receive the liquid drug from the reservoir 126. The system 100 may operate as a closed-loop system, an open-loop system, or as a hybrid system. In an exemplary closed-loop system, the controller 109 may direct operation of the device 105 without input from the controller 102, and may receive BG level signal 112 from the sensor 108. The sensor 108 may be housed within the device 105 or may be housed in a separate device and communicate wirelessly directly with the device 105.

As further shown, the system 100 may include a needle deployment component 128 in communication with the controller 102 or the controller 109. The needle deployment component 128 may include a needle/cannula 129 deployable into the patient 103 and may have one or more holes at a distal end thereof. The device 105 may be connected to the needle/cannula 129 by a fluid path component 130. The fluid path component 130 may be of any size and shape and may be made from any material. The fluid path component 130 can allow fluid, such as the liquid drug 125 in the reservoir 126, to be transferred to the needle/cannula 129.

The controller 102/109 may be implemented in hardware, software, or any combination thereof. The controller 102/109 may, for example, be a processor, a logic circuit or a microcontroller coupled to a memory. The controller 102/109 may maintain a date and time as well as other functions (e.g., calculations or the like) performed by processors. The controller 102/109 may be operable to execute an artificial pancreas (AP) algorithm stored in memory (not shown) that enables the controller 102/109 to direct operation of the pump 104. For example, the controller 102/109 may be operable to receive an input from the sensor 108, wherein the input indicates an automated insulin delivery (AID) application setting. Based on the AID application setting, the controller 102/109 may modify the behavior of the pump 104 and resulting amount of the liquid drug 125 to be delivered to the patient 103 via the device 105.

In some embodiments, the sensor 108 may be, for example, a continuous glucose monitor (CGM). The sensor 108 may be physically separate from the pump 104, or may be an integrated component within a same housing thereof. The sensor 108 may provide the controller 102 with data indicative of measured or detected blood glucose levels of the user.

The power element 123 may be a battery, a piezoelectric device, or the like, for supplying electrical power to the device 105. In other embodiments, the power element 123, or an additional power source (not shown), may also supply power to other components of the pump 104, such as the controller 102, memory, the sensor 108, and/or the needle deployment component 128.

In an example, the sensor 108 may be a device communicatively coupled to the controller 102 and may be operable to measure a blood glucose value at a predetermined time interval, such as approximately every 5 minutes, 10 minutes, or the like. The sensor 108 may provide a number of blood glucose measurement values to the AP application.

In some embodiments, the pump 104, when operating in a normal mode of operation, provides insulin stored in the reservoir 126 to the patient 103 based on information (e.g., blood glucose measurement values, target blood glucose values, insulin on board, prior insulin deliveries, time of day, day of the week, inputs from an inertial measurement unit, global positioning system-enabled devices, Wi-Fi-enabled devices, or the like) provided by the sensor 108 or other functional elements of the pump 104. For example, the pump 104 may contain analog and/or digital circuitry that may be implemented as the controller 102/109 for controlling the delivery of the drug or therapeutic agent. The circuitry used to implement the controller 102/109 may include discrete, specialized logic and/or components, an application-specific integrated circuit, a microcontroller or processor that executes software instructions, firmware, programming instructions or programming code enabling, for example, an AP application stored in memory, or any combination thereof. For example, the controller 102/109 may execute a control algorithm and other programming code that may make the controller 102/109 operable to cause the pump to deliver doses of the drug or therapeutic agent to a user at predetermined intervals or as needed to bring blood glucose measurement values to a target blood glucose value. The size and/or timing of the doses may be pre-programmed, for example, into the AP application by the patient 103 or by a third party (such as a health care provider, a parent or guardian, a manufacturer of the wearable drug delivery device, or the like) using a wired or wireless link.

Although not shown, in some embodiments, the sensor 108 may include a processor, memory, a sensing or measuring device, and a communication device. The memory may store an instance of an AP application as well as other programming code and be operable to store data related to the AP application.

In various embodiments, the sensing/measuring device of the sensor 108 may include one or more sensing elements, such as a blood glucose measurement element, a heart rate monitor, a blood oxygen sensor element, or the like. The sensor processor may include discrete, specialized logic and/or components, an application-specific integrated circuit, a microcontroller or processor that executes software instructions, firmware, programming instructions stored in memory, or any combination thereof.

Figure 2A:
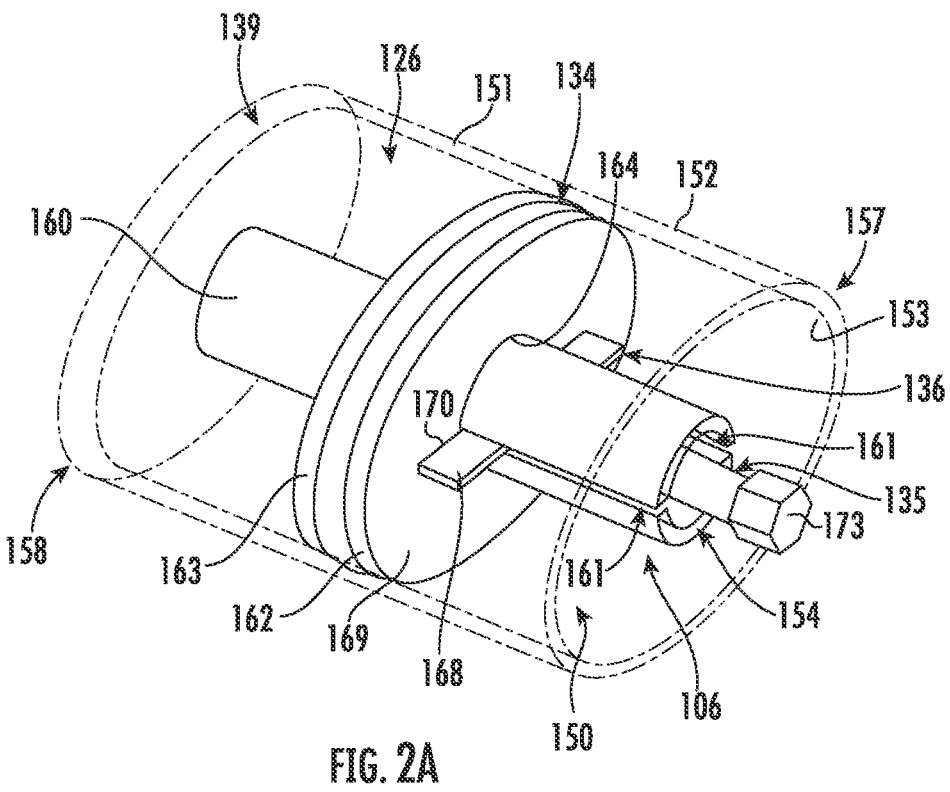
FIG. 2A illustrates a perspective view of a drive mechanism of a delivery pump device, according to embodiments of the present disclosure.
Figure 2B:
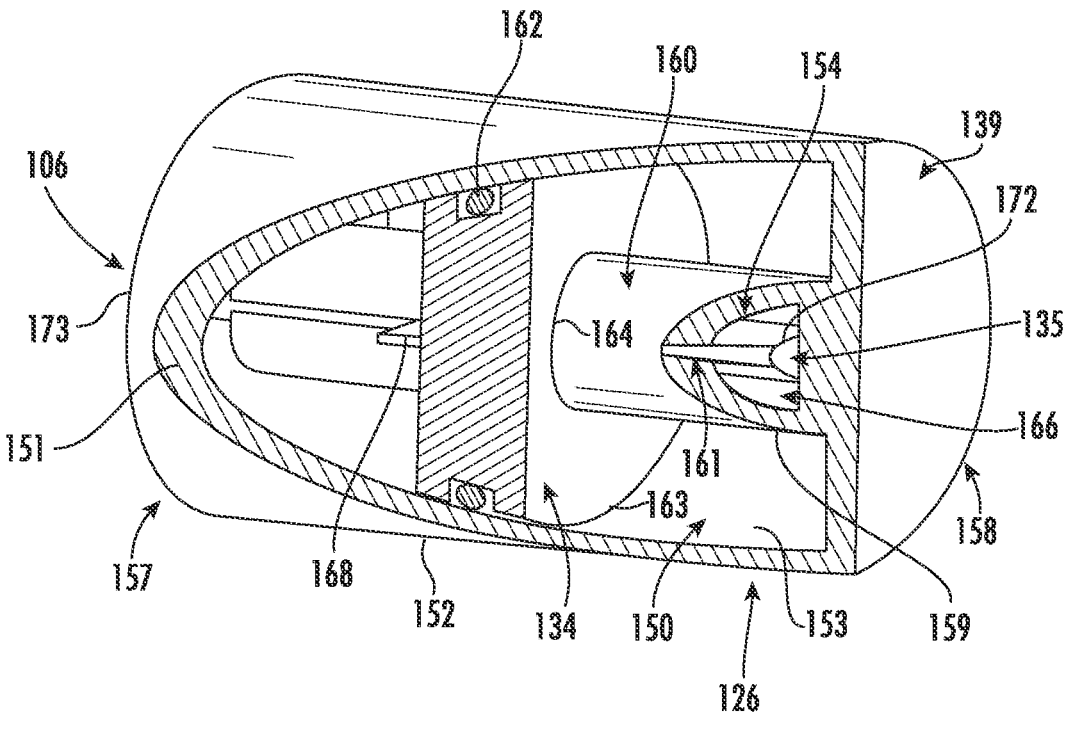
FIG. 2B illustrates a partial cutaway perspective view of the drive mechanism of FIG. 2A, according to embodiments of the present disclosure.

Turning now to FIGS. 2A-2B, the drive mechanism 106 according to embodiments of the present disclosure will be described in greater detail. As shown, the drive mechanism 106 may be positioned within an interior chamber 150 of the housing 139 of the reservoir 126. The housing 139 may include an outer wall 151 defining the interior chamber 150, wherein the outer wall 151 includes an exterior surface 152 opposite an interior surface 153. Although non-limiting, the housing 139 may be an oval-shaped cylinder including a first end 157 opposite a second end 158.

In some embodiments, the housing 139 may include a core shaft 154 within the interior chamber 150. As shown, the core shaft 154 may include one or more slits 161 extending axially along a length of a wall defining the core shaft 154. A sealing member 160 (e.g., a thin polyethylene film) may be disposed along an exterior surface 159 of the core shaft 154. As shown, the sealing member 160 may cover or extend across each slit 161 of the core shaft 154. In various embodiments, the sealing member 160 may cover all or only a part of the exterior surface 159 of the core shaft 154. In other embodiments, the sealing member 160 may be located along an interior surface of the core shaft 154, and/or may be positioned directly within slit(s) 160. In such cases, avoidance of tearing of the sealing member 160 as well as a better seal may be achieved between an interior surface 164 of the piston head 134 and the core shaft 154, than if the sealing member 160 were positioned on an exterior surface 159 of the core shaft 154.

As further shown, the drive mechanism 106 may include the piston head 134 disposed within the interior chamber 150 of the housing 139. In some embodiments, the piston head 134 may include a first sealing ring 162 (e.g., O-ring) extending circumferentially about an outer surface 163. The first sealing ring 162 may be in contact with the interior surface 153 of the outer wall 151 to create a liquid-tight seal therebetween. Although not shown, the piston head 134 may further include a second sealing ring extending circumferentially about an interior surface 164. The second sealing ring may provide a liquid-tight seal between the interior surface 164 and the core shaft 154 (or the sealing member 160 surrounding the core shaft 154).

The drive mechanism 106 may further include the lead screw 135 extending within an interior 166 of the core shaft 154. The lead screw 135 may include a first end 172 located at a bottom of the interior 166 of the core shaft 154 and a second end 173 extending outside of the core shaft 154. Although not shown, the second end 173 of the lead screw 135 may be coupled to a clutch mechanism, a ratchet mechanism, or other device operable to rotate the lead screw 135. In some embodiments, the lead screw 135 is coupled to the drive nut 136, which may include one or more blades 168 extending through the slit 161 of the core shaft 154. The blade(s) 168 may be a metal portion of the drive nut 136, oriented perpendicular to the lead screw 135. As shown, the blade(s) 168 may be in direct physical contact with an outer face 169 of the piston head 134. The blade(s) 168 may include a sharp portion that can cut through sealing member 160 and a non-sharp or blunt portion that is in direct physical contact with an outer surface 169 of the piston head 134. Alternatively, the blade(s) 168 can have a uniform shape along its entire front edge (e.g., the entire front edge may be approximately the same sharpness or bluntness). During use, as the lead screw 135 rotates, the drive nut 136 moves towards the second end 158 of the housing 139, which causes a leading edge 170 of the blade 168 to slice through the sealing member 160 and press against the outer face 169 of the piston head 134 to move the piston head 134 down (i.e., towards the second end 158) within the interior chamber 150. In some embodiments, a portion of the leading edge 170 of the blade 168 may be sharpened to better slice through the sealing member 160.

Figure 3A:
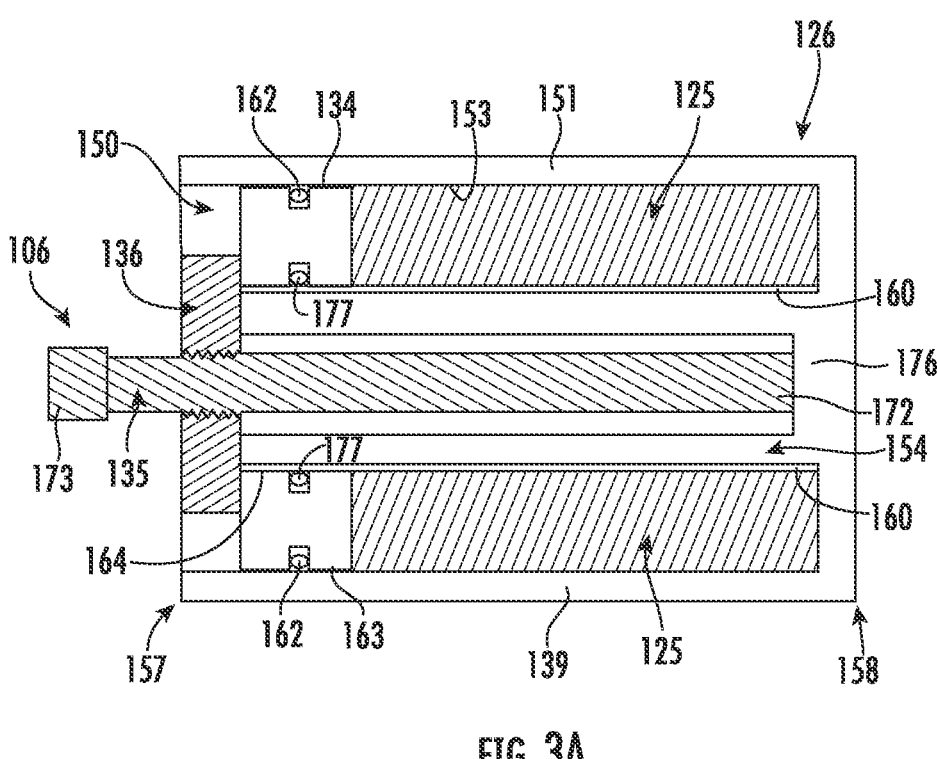
FIGS. 3A-3C are side cross-sectional views illustrating use of the drive mechanism, according to embodiments of the present disclosure.
Figure 3B:
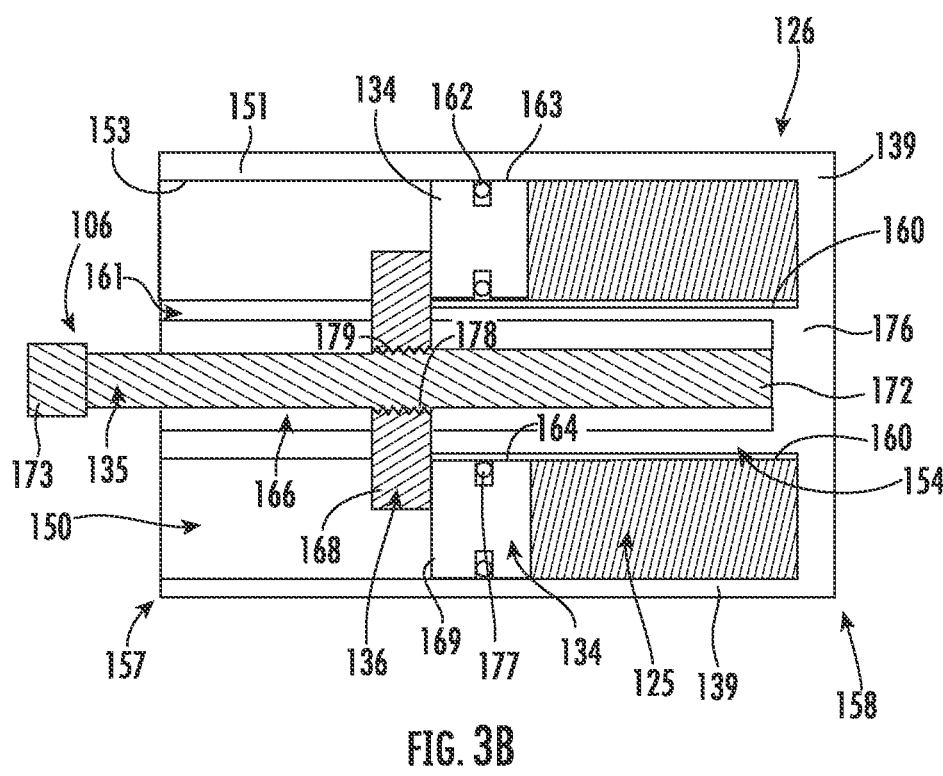
Figure 3C:
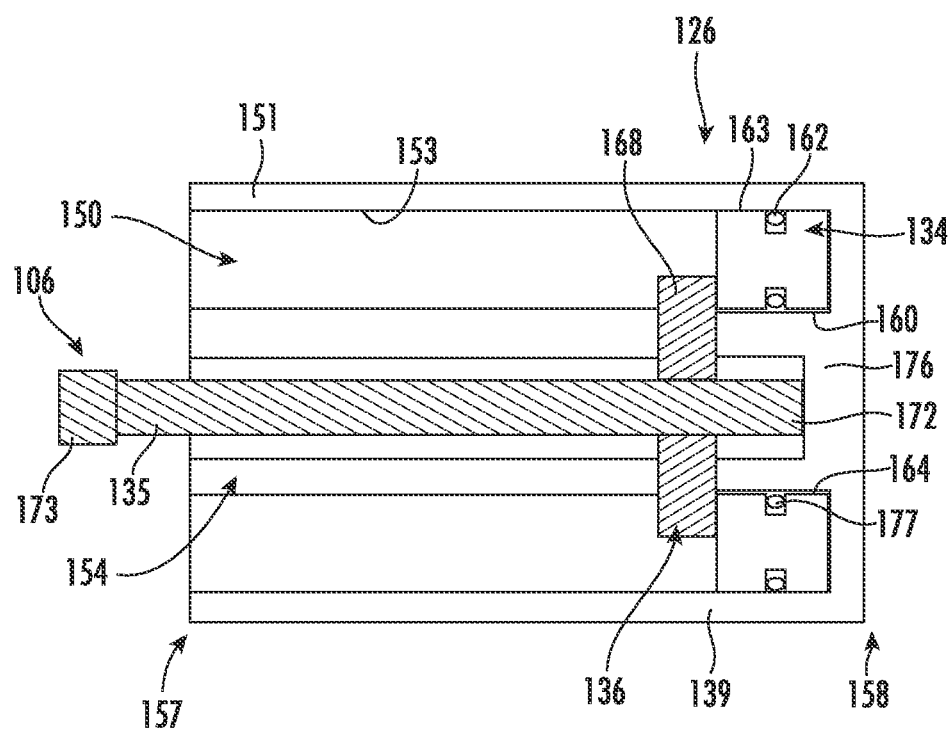

Turning now to FIGS. 3A-3C, operation of the drive mechanism 106 according to embodiments of the present disclosure will be described in greater detail. In FIG. 3A, which demonstrates the reservoir 126 filled with the liquid drug 125, the piston head 134 and the drive nut 136 are positioned proximate the first end 157 of the housing 139 of the reservoir 126. The interior chamber 150 may be filled with the liquid drug 125 by opening an inlet port (not shown) of the reservoir 126 and pumping in the liquid drug 125 under sufficient hydraulic pressure to retract the piston head towards the first end 157 of the housing 139. In some embodiments, the hydraulic pressure may cause the piston head 134 to rotate about the lead screw 135 until the piston head 134 is positioned proximate the second end 173 of the lead screw 135. As shown, the first end 172 of the lead screw 135 may be positioned in contact with, or adjacent to, a base wall 176 defining a bottom of the core shaft 154.

As further shown, the piston head 134 may include the first sealing ring 162 extending circumferentially about the outer surface 163, and a second sealing ring 177 extending circumferentially about the interior surface 164. The first sealing ring 162 may be in contact with the interior surface 153 of the outer wall 151 to create a liquid-tight seal therebetween. The second sealing ring 177 may provide a liquid-tight seal between the interior surface 164 and the sealing member 160 surrounding the core shaft 154.

As shown in FIG. 3B, to dispense the liquid drug 125 from the reservoir 126, the lead screw 135 is rotated within the interior 166 of the core shaft 154, which causes the drive nut 136 to move axially from the second end 173 of the lead screw 135 toward the first end 172 of the lead screw 135. In some embodiments, the lead screw 135 may include external threading 178 engaged with corresponding internal threading 179 of the drive nut 136 to force the drive nut 136 into the outer face 169 of the piston head 134. As the drive nut 136 and the piston head 134 move towards the second end 158 of the housing 139, the blade 168 of the drive nut 136 moves along the slit 161 and slices through the sealing member 160, which allows the drive nut 136 and the piston head 134 to continue to travel. Although the blade 168 creates an opening in the sealing member 160, the first and second sealing rings 162, 177 are positioned ahead of the blade 168, along a direction of travel of the drive nut 136, which prevents the liquid-tight seal of the reservoir 126 from being broken. As shown, the first end 172 of the lead screw 135 may remain in place proximate the base wall 176 of the core shaft 154 as the piston head 134 moves.

Rotation of the lead screw 135 may continue until the piston head 134 is moved to the end of the interior chamber 150 of the housing 139, as demonstrated in FIG. 3C. In this position, the drive mechanism 106 has fully expelled the liquid drug 125 from the reservoir 126.

Figure 4:
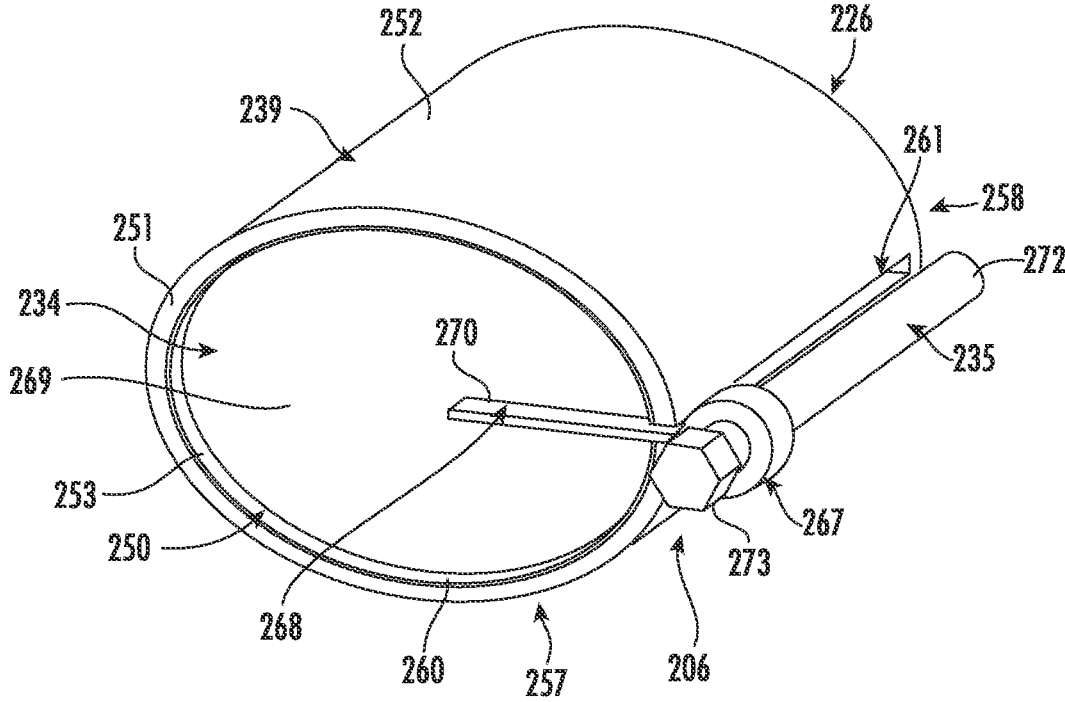
FIG. 4 illustrates a perspective view of a drive mechanism of a delivery pump device, according to embodiments of the present disclosure.

Turning now to FIG. 4, another drive mechanism 206 according to embodiments of the present disclosure will be described in greater detail. The drive mechanism 206 may be part of a wearable or on-body drug delivery device and/or an analyte sensor attached to the skin of a patient, such as the system 100 described above. As shown, the drive mechanism 206 may be coupled to a housing 239 of a reservoir 226. The housing 239 may include an outer wall 251 defining an interior chamber 250, wherein the outer wall 251 includes an exterior surface 252 opposite an interior surface 253. Although non-limiting, the housing 239 may be an oval-shaped cylinder including a first end 257 opposite a second end 258.

In some embodiments, a sealing member 260 (e.g., a thin polyethylene film) may be disposed along the interior surface 253 of the outer wall 251 of the housing 239. In other embodiments, the sealing member 260 may be disposed along the exterior surface 252 of the outer wall 251 of the housing 239, or directly within slit 261, and the sealing member may be a wax material, a painted-on coating, or flexible polycarbonate material. The sealing member 260 may cover all or only a part of the interior surface 253, exterior surface 252, or slit 261. As shown, the sealing member 260 may extend across a slit 261 formed through the outer wall 251 of the housing 239.

As further shown, the drive mechanism 206 may include a piston head 234 disposed within the interior chamber 250 of the housing 239. In some embodiments, the piston head 234 may include one or more sealing rings (not shown) extending circumferentially about an outer surface thereof. The sealing ring may be in contact with an interior of the sealing member 260 to create a liquid-tight seal therebetween.

The drive mechanism 206 may further include a lead screw 235 extending adjacent/external to the outer wall 251 of the housing 239. The lead screw 235 may include a first end 272 located adjacent the second end 258 of the housing 239 and a second end 273 located adjacent the first end 257 of the housing 239. Although not shown, the second end 273 of the lead screw 235 may be coupled to a clutch mechanism or other device operable to rotate the lead screw 235. In some embodiments, the lead screw 235 is coupled to a drive nut 267, which may include one or more blades 268 extending through the slit 261 of the outer wall 251 of the housing 239. As shown, the blade 268 may extend perpendicular to the lead screw 235. In some embodiments, the blade 268 may be directly adjacent an outer face 269 of the piston head 234. During use, as the lead screw 235 rotates, the drive nut 267 moves axially along the lead screw 235 towards the second end 258 of the housing 239, which causes a leading edge 270 of the blade 268 to slice through the sealing member 260. The blade 268 presses against the outer face 269 of the piston head 234 to move the piston head 234 down (i.e., towards the second end 258) within the interior chamber 250. In some embodiments, a portion of the leading edge 270 of the blade 268 may be sharpened to better slice through the sealing member 260.

Figure 5A:
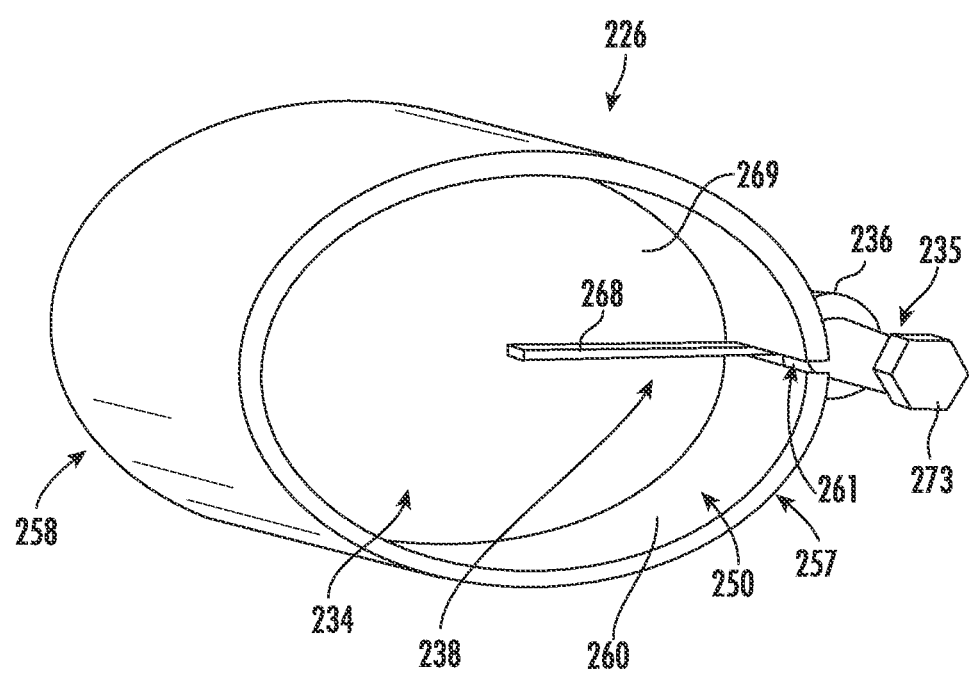
FIGS. 5A-5B are perspective views illustrating operation of the drive mechanism of FIG. 4, according to embodiments of the present disclosure.
Figure 5B:
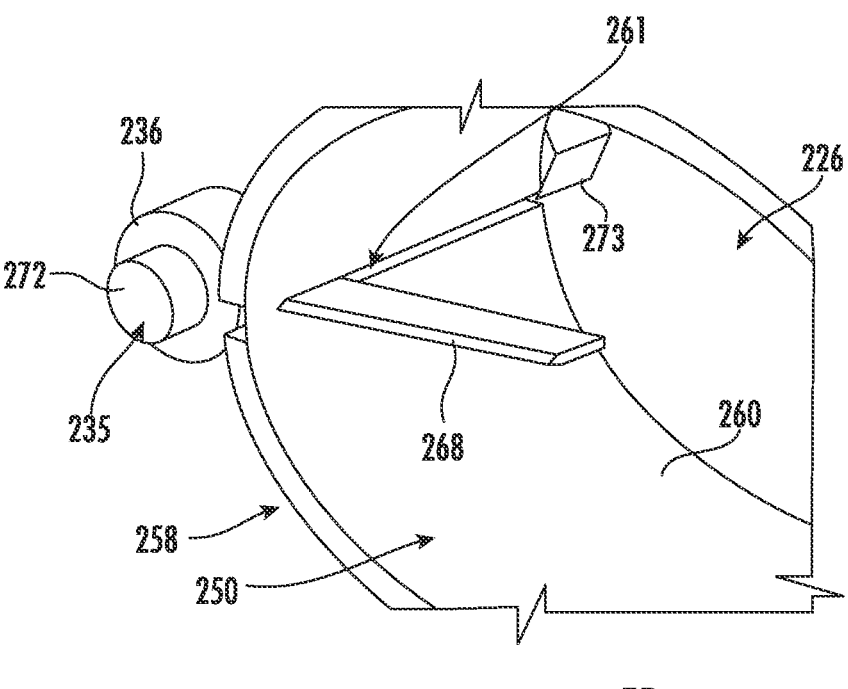

Turning now to FIGS. 5A-5B, operation of the drive mechanism 206 according to embodiments of the present disclosure will be described in greater detail. To dispense the liquid drug from the reservoir 226, the lead screw 235 is rotated, which causes the drive nut 236 to move axially from the second end 273 of the lead screw 235 towards the first end 272 of the lead screw 235. In some embodiments, the lead screw 235 may include external threading engaged with corresponding internal threading of the drive nut 236 to force the drive nut 236 into the outer face 269 of the piston head 234 (not shown in FIG. 5B for clarity). As the drive nut 236 and the piston head 234 move towards the second end 258 of the housing 239, the blade 268 of the drive nut 236 moves along the slit 261 and slices through the sealing member 260, which allows the drive nut 236 and piston head 234 to continue to travel. Rotation of the lead screw 235 may continue until the piston head 234 is moved to the end of the interior chamber 250 and the liquid drug has been fully expelled from the reservoir 226.

FIG. 6 illustrates an example process 300 according to embodiments of the present disclosure. At block 301, the process 300 may include providing a reservoir configured to store a liquid drug, the reservoir including a housing having an outer wall defining an interior chamber, a sealing member within the interior chamber, and a slit through the housing, wherein the sealing member is configured to extend across the slit. In some embodiments, the reservoir is part of a wearable drug delivery device. In some embodiments, the sealing member is a thin film (e.g., polyethylene, low-density polyethylene, high-chlorinated polyethylene), or a wax or other material suitable for filling a slit in the housing.

In some embodiments, the housing of the reservoir includes a core shaft within the interior chamber, wherein the sealing member is formed along an exterior surface of the core shaft. The lead screw of the drive mechanism may extend within an interior of the core shaft, wherein the slit is formed through the core shaft.

In some embodiments, the slit may be formed through the outer wall of the housing, and the sealing member may be disposed along an interior surface of the outer wall. As such, the sealing member may extend across the slit to enclose the interior chamber.

At block 302, the process 300 may further include coupling a drive mechanism of a delivery pump device to the reservoir, the drive mechanism including a piston head disposed within the interior chamber of the housing, and a lead screw coupled to a drive nut, wherein the drive nut comprises a blade adjacent the piston head. The blade may be positionable through the slit of the housing for engagement with the piston head and the sealing member. In some embodiments, the lead screw is positioned within the core shaft of the housing. In other embodiments, the lead screw is positioned adjacent/external to the outer wall of the housing. The blade of the drive nut may extend perpendicular to the lead screw. In some embodiments, the blade of the drive nut is directly adjacent to and/or in direct physical contact with an outer face of the piston head. In some embodiments, the lead screw may include external threading engaged with corresponding internal threading of the drive nut to force the drive nut into the outer face of the piston head.

In some embodiments, the method may include providing a first sealing ring about an outer surface of piston head and providing a second sealing ring about an interior surface of the piston head. The first sealing ring may be in direct physical contact with the interior surface of the outer wall of the housing, and the second sealing ring may be in direct physical contact with the sealing member.

At block 303, the process 300 may include rotating the lead screw to cause the drive nut to move axially along the lead screw between a first position and a second position to drive the liquid drug out of the reservoir. In the first position, the drive nut may be proximate a first end of the housing of the reservoir. In the second position, the drive nut may be proximate a second end of the housing of the reservoir. In some embodiments, the blade of the drive nut may cut through the sealing member as the drive nut moves between the first position and the second position.

As used herein, the algorithms or computer applications that manage blood glucose levels and insulin therapy may be referred to as an "artificial pancreas" algorithm-based system, or more generally, an artificial pancreas (AP) application. An AP application may be programming code stored in a memory device and that is executable by a processor, controller or computer device.

The techniques described herein for a drug delivery system (e.g., the system 100 or any components thereof) may be implemented in hardware, software, or any combination thereof. Any component as described herein may be implemented in hardware, software, or any combination thereof. For example, the system 100 or any components thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

Some examples of the disclosed devices may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosed subject matter were described above. It is, however, expressly noted that the present disclosed subject matter is not limited to those examples, but rather the intention is that additions and modifications to what was expressly described herein are also included within the scope of the disclosed subject matter. Moreover, it is to be understood that the features of the various examples described herein were not mutually exclusive and may exist in various combinations and permutations, even if such combinations or permutations were not made express herein, without departing from the spirit and scope of the disclosed subject matter. In fact, variations, modifications, and other implementations of what was described herein will occur to those of ordinary skill in the art without departing from the spirit and the scope of the disclosed subject matter. As such, the disclosed subject matter is not to be defined only by the preceding illustrative description.

Program aspects of the technology may be thought of as "products" or "articles of manufacture" typically in the form of executable code and/or associated data that is carried on or embodied in a type of machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of example examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A wearable drug delivery device, comprising:
a reservoir configured to store a liquid drug, the reservoir comprising:
  a housing including an outer wall defining an interior chamber;
  a sealing member; and
  a slit through at least a portion of the housing, wherein the sealing member seals the slit; and
a delivery pump device including a drive mechanism coupled to the reservoir for driving the liquid drug out of the reservoir, the drive mechanism comprising:
  a piston head disposed within the interior chamber of the housing; and
  a lead screw coupled to a drive nut, wherein the drive nut comprises a blade adjacent the piston head, and wherein the blade is within the slit of the housing and configured to move within the slit to cut the sealing member, wherein an entirety of the slit and an entirety of the blade are contained within the reservoir.

2. The wearable drug delivery device of claim 1, the housing of the reservoir comprising a core shaft within the interior chamber, wherein the sealing member is formed along an exterior surface of the core shaft, and wherein the lead screw of the drive mechanism extends within an interior of the core shaft.

3. The wearable drug delivery device of claim 2, wherein the slit is formed through the core shaft.

4. The wearable drug delivery device of claim 2, wherein the piston head includes a first sealing ring extending about an outer surface and a second sealing ring extending about an interior surface, and wherein the second sealing ring is in direct physical contact with the sealing member formed along the exterior surface of the core shaft.

5. The wearable drug delivery device of claim 1, wherein the blade of the drive nut extends perpendicular to or radially outward from the lead screw, and wherein the blade of the drive nut is in direct physical contact with an outer face of the piston head.

6. The wearable drug delivery device of claim 1, wherein the sealing member is a polyethylene film.

7. A wearable drug delivery device, comprising:
a reservoir configured to store a liquid drug, the reservoir comprising:
  a housing including an outer wall defining an interior chamber;
  a sealing member; and
  a slit through at least a portion of the housing, wherein the sealing member seals the slit; and
a delivery pump device including a drive mechanism coupled to the reservoir for driving the liquid drug out of the reservoir, the drive mechanism comprising:
  a piston head disposed within the interior chamber of the housing; and
  a lead screw coupled to a drive nut, wherein the drive nut comprises a blade adjacent the piston head, wherein the blade is within the slit of the housing and configured to move within the slit to cut the sealing member, wherein an entirety of the slit and an entirety of the blade are contained within the reservoir, and wherein the lead screw has external threading engaged with corresponding internal threading of the drive nut, and wherein rotation of the lead screw causes the blade to move axially along the lead screw.

8. The wearable drug delivery device of claim 7, the housing of the reservoir comprising a core shaft within the interior chamber, wherein the sealing member is formed along an exterior surface of the core shaft, wherein the lead screw of the drive mechanism extends within an interior of the core shaft, and wherein the slit is formed through the core shaft.

9. The wearable drug delivery device of claim 8, wherein the piston head includes a first sealing ring extending about an outer surface and a second sealing ring extending about an interior surface, wherein the second sealing ring is in direct physical contact with the sealing member formed along the exterior surface of the core shaft.

10. The wearable drug delivery device of claim 7, wherein the blade of the drive nut extends perpendicular to the lead screw, and wherein the blade of the drive nut is directly adjacent an outer face of the piston head.

11. A method, comprising:

providing a reservoir configured to store a liquid drug, the reservoir comprising:

a housing including an outer wall defining an interior chamber;

a sealing member; and a slit through the housing, wherein the sealing member seals the slit;

coupling a drive mechanism of a delivery pump device to the reservoir, the drive mechanism comprising:

a piston head disposed within the interior chamber of the housing; and a lead screw coupled to a drive nut, wherein the drive nut comprises a blade adjacent the piston head, and wherein the blade is within the slit of the housing and configured to move within the slit to cut the sealing member, wherein an entirety of the slit and an entirety of the blade are contained within the reservoir; and rotating the lead screw to cause the drive nut to move axially along the lead screw between a first position and a second position to force the liquid drug out of the reservoir.

12. The method of claim 11, further comprising:

providing the sealing member along an exterior surface of a core shaft of the housing, wherein the slit is formed through the core shaft; and cutting through the sealing member with the blade of the drive nut as the drive nut moves between the first position and the second position.

13. The method of claim 12, further comprising positioning the lead screw of the drive mechanism within an interior of the core shaft.

14. The method of claim 12, further comprising providing a first sealing ring about an outer surface of piston head and providing a second sealing ring about an interior surface of the piston head, wherein the second sealing ring is in direct physical contact with the sealing member formed along the exterior surface of the core shaft.

15. The method of claim 11, further comprising positioning the blade of the drive nut in direct physical contact with an outer face of the piston head, wherein the axial movement of the drive nut causes the piston head to move within the interior chamber of the housing.

* * * * *